(12) United States Patent
Herrlein et al.

(10) Patent No.: US 6,388,166 B1
(45) Date of Patent: *May 14, 2002

(54) DISPOSABLE ABSORBENT ARTICLES WITH CONTROLLED SKIN HYDRATION EFFECT

(76) Inventors: Mathais Kurt Herrlein; John Peter Lankhof, both of Procter & Gamble European Service GmbH, Sulzbacher Str. 40-50, 65824 Schwalbach/TS (DE); Muir Charles Robertson, Procter & Gamble Company, 6100 Center Hill Ave., Cincinnati, OH (US) 45224; Jose Dominguez-Staedke, Procter & Gamble European Service GmbH, Sulzbacher Str. 40-50, 65824 Schwalbach/TS (DE); Ivan Jean Olliver, Procter & Gamble European Service GmbH, Sulzbacher Str. 40-50, 65824 Schwalbach/TS (DE); Karl Michael Schumann, Procter & Gamble European Service GmbH, Sulzbacher Str. 40-50, 65824 Schwalbach/TS (DE)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/155,469
(22) PCT Filed: Mar. 25, 1997
(86) PCT No.: PCT/US97/04807
§ 371 Date: Sep. 29, 1998
§ 102(e) Date: Sep. 29, 1998
(87) PCT Pub. No.: WO97/36562
PCT Pub. Date: Oct. 9, 1997

(30) Foreign Application Priority Data
Mar. 29, 1996 (GB) ............................................ 96105023

(51) Int. Cl.[7] ................................................. A61F 13/15
(52) U.S. Cl. ........................ 604/367; 604/378; 604/358
(58) Field of Search .................................. 604/367, 358

(56) References Cited

U.S. PATENT DOCUMENTS

| 4,609,584 | A | * | 9/1986 | Cutler et al. ................. 428/156 |
| 4,681,580 | A | * | 7/1987 | Reising et al. ............... 604/385 |
| 4,857,065 | A | * | 8/1989 | Seal ............................ 604/368 |
| 4,883,480 | A | * | 11/1989 | Huffman et al. ......... 604/385.1 |
| 5,037,409 | A | | 8/1991 | Chen et al. |
| 5,558,658 | A | * | 9/1996 | Menard et al. .......... 604/385.1 |
| 5,810,797 | A | * | 9/1998 | Menard et al. ............. 604/378 |

FOREIGN PATENT DOCUMENTS

EP    0 422 504 A2    4/1991

\* cited by examiner

Primary Examiner—John G. Weiss
Assistant Examiner—Michael G Bogart
(74) Attorney, Agent, or Firm—Joan B. Cunningham; Ken K. Patel; Steven W. Miller

(57) ABSTRACT

This invention is a disposable absorbent article (20) covering certain parts of the body of the wearer and comprising a loading area, a storage area, as well as a chassis area, whereby the absorbent article has a specific skin hydration value, calculated from the individual skin hydration values of the respective areas.

7 Claims, 3 Drawing Sheets

DISPOSABLE ABSORBENT ARTICLES WITH CONTROLLED SKIN HYDRATION EFFECT

The present invention relates to disposable absorbent articles such as diapers, incontinence articles, sanitary towels, training pants and the like, and in particular to the control of their hydration effect on the human skin.

BACKGROUND OF THE INVENTION

Disposable, absorbent articles such as diapers, incontinence articles, sanitary towels, training pants and the like are well know in the art. Typically, disposable absorbent articles comprise a liquid previous topsheet that faces the wearers body, a liquid impervious backsheet that faces the wearers clothing, an absorbent core interposed between the liquid previous topsheet and the backsheet, and means to keep the core in fixed relation to the wearers body.

The absorbent core needs to be capable of acquiring, distributing, and storing discharges initially deposited on the topsheet of the absorbent article. Preferably the design of the absorbent core is such that the core acquires the discharges substantially immediately after they have been deposited on the topsheet of the absorbent article, with the intention that the discharges do not accumulate on or run off the surface of the topsheet, since this may result in inefficient fluid containment by the absorbent article which may lead to wetting of outer garments and discomfort for the wearer. After the insult, it is an essential functionality of the absorbent article to retain the discharged fluids firmly so as to avoid over-hydration of the skin of the wearer. If the absorbent article is not well functioning in this respect, liquid coming from the absorbent core back to the skin—also often called "rewet"—can have detrimental effects on the condition of the skin, which can for example be observed by skin irritations.

There, have been many attempts to improve the fluid handling properties of absorbent articles or cores, in particular when further requirements were brought up such as a desired reduction of product bulkiness or thickness.

Several patent publications deal with such improvements by adding specially treated cellulosic material. For example U.S. Pat. No. 4,898,642 of Moore et al. discloses specially twisted, chemically stiffened cellulosic fibres and absorbent structures made therefrom. EP 0 640 330 (Bewick-Sonntag) et al. discloses the use of such fibres in a specific arrangement with specific superabsorbent materials. EP 0 397 110 (Latimer) discloses an absorbent article comprising a surge management region for improved fluid handling, having specific basis weights, acquisition times and residual wetness.

EP 0 312 118 (Meyer) discloses an absorbent article with a fibrous topsheet with larger pores than the pores of the underlying transport layer, which in turn has larger pores than the underlying absorbent body. Further, the transport layer has to have a hydrophilicity which is less than the one of the absorbent core, and may generally be characterized as being substantially hydrophobic.

In EP 0 312 118 it is said that some liquid might remain in the transport layer and in the topsheet, so as to cause a wet feel on the surface. In order to overcome this problem, it is proposed in EP 0 312 118 to exploit the resilient compressibility of the transport layer, such that in use under the pressure exerted by the baby, the pores become smaller and then can dry out the topsheet and transport the fluid away into the underlying absorbent body.

In accordance with the development direction of these various approaches, the tools to assess the performance of such structures were generally aiming at measuring the liquid transfer—either from the surface of the absorbent structure into the structure itself often referred to as the acquisition, or within the absorbent structure referred to as distribution.

On the other hand the rewetting from the absorbent structure has been tested, either by using in-vivo methods or by using laboratory tests.

The in-vivo methods have in common, that they assess directly the condition of the skin of the wearer of an absorbent article either under real in-use loadings or possibly with artificially loaded articles, which are for example worn on the forearm of a test person for a certain period.

Elsner et al. provides a comprehensive overview of such methods in "Bio-engineering of the: Water and Stratum Corneum", CRC Press, 1994. The most relevant methods are the "Transepidermal Water Loss" (often abbreviated TEWL) measuring the moisture evaporation from the skin; methods to measure the electrical properties like capacitance, impedance, or conductance of the skin, which depend strongly on the moisture content, such as with the NOVAMETER (capacitance of skin) the CORNEOMETER or other instruments. Elsner further discusses in detail the negatives of both too dry and too wet (overhydrated) skin, and the risks of higher occurrence of skin irritations or even damages, which can be most easily detected by "redmarking" of the skin, in particular, when the over-hydration occurs in combination with mechanical stress such as chafing.

However, all in-vivo methods have in also common, that the comparison of absorbent structures or articles for development purposes is cumbersome. Apart from the fact of needing test persons as such, individual parameters of the test persons—such as varying reaction to certain room conditions as temperature or relative humidity—are responsible for a large variability in the test results. In order to still get meaningful data, the number of test persons must be increased to substantial amounts.

Hence, significant effort has already been put against evaluating absorbent articles and structures under reproducible and easy to execute laboratory conditions, whereby mostly the human skin is replaced by standardized fluid pick-up filter paper. Essentially, these methods are based on the "capillary rewet" principle, whereby a test sample is loaded with a certain amount of test fluid, such as synthetic urine. After a certain time such as to allow for equilibration and preferably under a certain pressure, the pick up filter paper as "skin replacement" is placed on top of the surface of the loaded structure for a certain time, under a certain pressure. The pick-up filter paper is well defined such as by porosity, basis weight, or absorbency. Due to the capillary forces of its pores, it is sucking up readily available moisture (i.e. "free" moisture not being bound such as through superabsorbent materials or in smaller pores than the ones of the pick-up paper) from the surface of the test specimen and the weight increase is a measure for the "rewet" performance of the absorbent article.

Optionally, this test procedure can be combined with other fluid handling evaluation protocols, for example a "post-acquisition-rewet-test" indicates, that during the first part of the combined protocol the fluid acquisition behaviour of the test specimen is studied, whereas the rewet assessment is then carried out in the second part of the test.

A number of such tests have been described, such as in WO 93/02 188 (Guidotti et al.); EP-0 039 974 (Mullane); EP 0 278 601 (Kobayashi); EP 0 539 703 (Hanson).

However, these tests have significant drawback, in so far as they are only sensitive to liquid moisture, which is present in capillaries larger then the capillaries of the pick-up medium. In particular upon development of better absorbent products, it has been found that not only the small amounts of liquid in relatively small pores (i.e. smaller than the pores of the filter pick up paper) can still contribute significantly to the overhydration of the skin of the wearer, but that also the moisture released by the skin itself in the form of sweat can have significant negative effects on overhydration of the skin, such as when covered with an impermeable material. This latter situation is often referred to as "occlusion", and of particular relevance for the non-absorbent regions in the absorbent article, often referred to as "chassis" or "peripheral" elements.

Another approach to assess the performance of such articles has been proposed by Lask et al. in EP-B-312919, whereby the surface moisture e.g. of an absorbent article is correlated to the reflection and scattering of a light beam. However, also this test is only directed towards the liquid moisture of the surface, and—even if it might have less limitations with respect to capillary size at the lower detection limit—is relying on essentially isotropic and homogeneous properties throughout the topsheet layer.

With improvements in the performance of absorbent articles, the ability of the known methods above to distinguish different products has decreased, such products achieving practically identical performance in said test, even though significant differences were detected by the user of the absorbent articles.

It has now been discovered that absorbent articles can be provided with hitherto unprecedented performance with respect to controlling the impact of the absorbent article on the skin hydration.

This is achieved by relying on a new tool for realistically and efficiently differentiating the absorbent articles with respect to their impact on the skin hydration. This is further achieved by not only focusing on the skin hydration impact of the absorbent article in zones which are either directly loaded with the liquid bodily discharges such as urine, menstrual fluids, or fecal materials of sufficiently high liquid content, but also in the zones of the absorbent article which are generally not being wetted by such liquids.

SUMMARY OF THE INVENTION

The present inventions aims at providing a disposable absorbent article covering certain parts of the body of the wearer and comprising distinct areas including a loading area, a storage area and a chassis area, whereby the absorbent article has a Skin Hydration Value of less than 1300, preferably less than 600, more preferably less than 300 as defined by the method described hereinafter; said Skin Hydration Value of the total article reflects the impact of the individual Skin Hydration Values of the respective areas of the articles; the definition of said individual Skin Hydration Value according to methods specific to the area, represents another aspect of the present invention.

DETAILED DESCRIPTION OF THE INVENTION

Absorbent Articles

As used herein, the term "absorbent articles" refers to devices which absorb and contain body exudates, and, more specifically, refers to devices which are placed against or in proximity to the body of the wearer to absorb and contain the various exudates discharged from the body. Such exudates comprise the body discharges for the release of which the absorbent article is primarily worn, such as urine and faeces for baby diapers, faeces and/or urine for adult incontinence products, menstrual fluids for catamenial products and so on. However, in the context of this invention, also secondary discharges can be subject of absorption of the articles, such discharges being an effect of the article being worn, and which are generally sweat.

The term "disposable" is used herein to describe absorbent articles which are not intended to be laundered or otherwise restored or reused as an absorbent article (i.e., they are intended to be discarded after a single use and, preferably, to be recycled, composted or otherwise disposed of in an environmentally compatible manner).

An absorbent article generally comprises an absorbent core (which may consist of sub-structures);

a fluid previous topsheet;

a fluid impervious backsheet;

optionally further features like closure elements or elastification.

Figure 1:
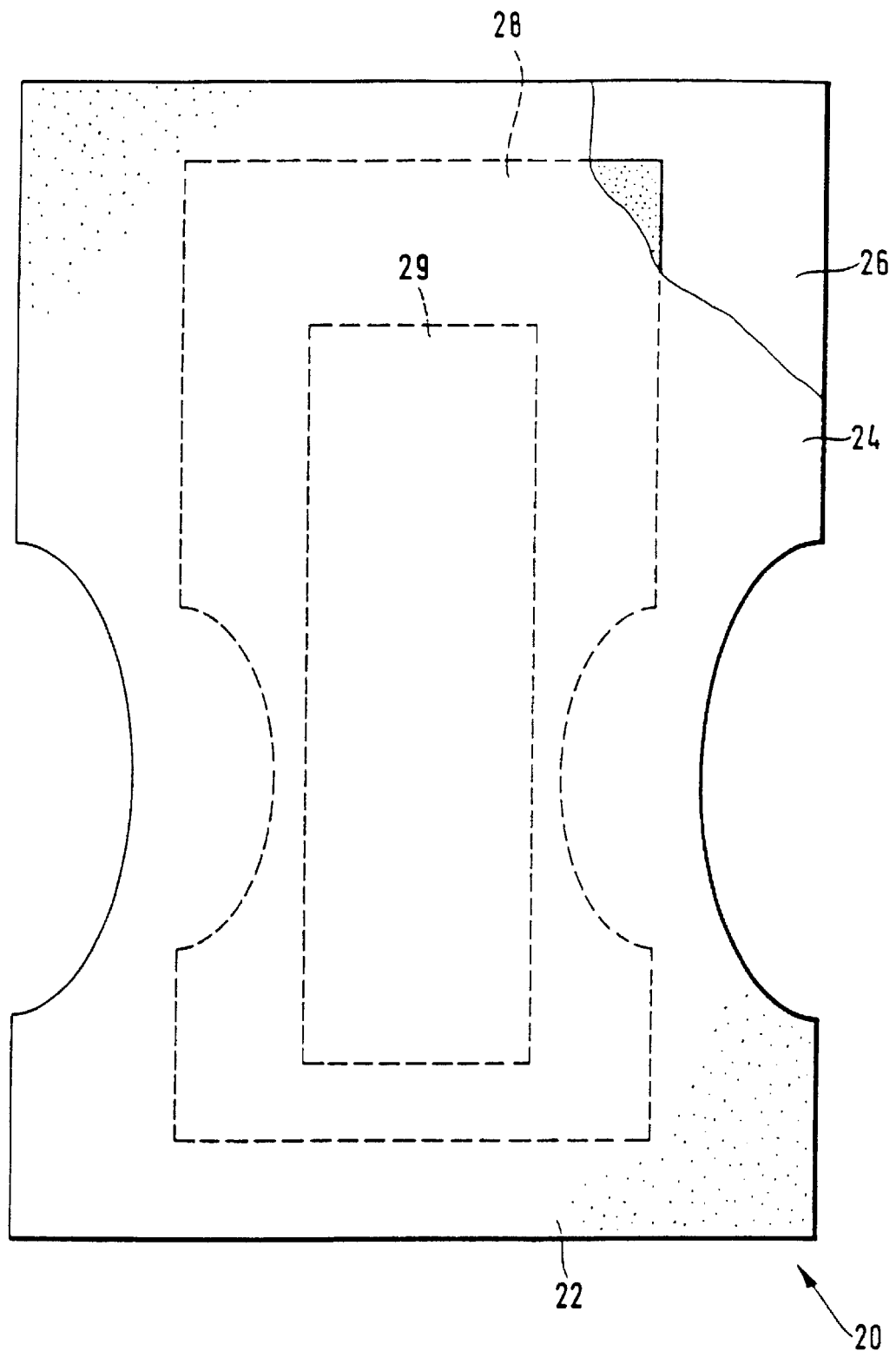
FIG. 1 exemplifies a simplified absorbent article, exemplifying a diaper.

A specific embodiment of an absorbent article of the present invention is the disposable absorbent article, diaper 20, shown in FIG. 1. As used herein, the term "diaper" refers to an absorbent article generally worn by infants and incontinent persons that is worn about the lower torso of the wearer. It should be understood, however, that the present invention is also applicable to other absorbent articles such as incontinent briefs, incontinent undergarments, diaper holders and liners, feminine hygiene garments, and the like.

FIG. 1 is a plan view of the diaper 20 in its flat-out, uncontracted state (i.e. with elastic induced contraction pulled out) with portions of the structure being cut-away to more clearly show the construction of the diaper 20 and with the portion of the diaper 20 which faces or contacts the wearer, the inner surface, oriented towards the viewer. As shown in FIG. 1, the diaper 20 preferably comprises a liquid previous topsheet 24; a liquid impervious backsheet 26 joined with the topsheet 24; an absorbent core 28 positioned between the topsheet 24 and the backsheet 26. If not specified differently, the term "upper" refers to the part of a structure directed towards the wearer of the article, "lower" directs away from the wearer.

FIG. 1 shows a preferred embodiment of the diaper 20 in which the topsheet 24 and the backsheet 26 have length and width dimensions generally larger than those of the absorbent core 28. The topsheet 24 and the backsheet 26 extend beyond the edges of the absorbent core 28 to thereby form the periphery 22 of the diaper 20. While the topsheet 24, the backsheet 26, and the absorbent core 28 may be assembled in a variety of well known configurations, preferred diaper configurations are described generally in U.S. Pat. No. 3,860,003 entitled "Contractable Side Portions for Disposable Diaper" which issued to Kenneth B. Buell on Jan. 14, 1975; and U.S. patent application Ser. No. 07/715,152, allowed, "Absorbent Article With Dynamic Elastic Waist Feature Having A Predisposed Resilient Flexural Hinge", Kenneth B. Buell et al. filed Jun. 13, 1991.

The backsheet 26 is positioned adjacent the garment surface of the absorbent core 28 and is preferably joined thereto by attachment means (not shown) such as those well known in the art. For example, the backsheet 26 may be secured to the absorbent core 28 by a uniform continuous layer of adhesive, a patterned layer of adhesive, or an array of separate lines, spirals, or spots of adhesive. Adhesives which have been found to be satisfactory are manufactured by H. B. Fuller Company of St. Paul, Minn. and marketed as HL-1258. The attachment means will preferably comprise an open pattern network of filaments of adhesive as is disclosed in U.S. Pat. No. 4,573,986 entitled "Disposable Waste-Containment Garment", which issued to Minetola et al. on Mar. 4, 1986, more preferably several lines of adhesive filaments swirled into a spiral pattern such as is illustrated by the apparatus and methods shown in U.S. Pat. No. 3,911,173 issued to Sprague, Jr. on Oct. 7, 1975; U.S. Pat. No. 4,785,996 issued to Ziecker, et al. on Nov. 22, 1978; and U.S. Pat. No. 4,842,666 issued to Werenicz on Jun. 27, 1989. Alternatively, the attachment means may comprise heat bonds, pressure bonds, ultrasonic bonds, dynamic mechanical bonds, or any other suitable attachment means or combinations of these attachment means as are known in the art.

The backsheet 26 is impervious to liquids (e.g. urine) and is often manufactured from a thin plastic film, although other flexible liquid impervious materials may also be used. As used herein, the term "flexible" refers to materials which are compliant and will readily conform to the general shape and contours of the human body. The backsheet 26 prevents the exudates absorbed and contained in the absorbent core 28 from wetting articles which contact the diaper 20 such as bed-sheets and undergarments. The backsheet 26 may thus comprise a woven or nonwoven material, polymeric films such as thermoplastic films of polyethylene or polypropylene, or composite materials such as a film-coated nonwoven material. Often, the backsheet is a thermoplastic film having a thickness of from about 0.012 mm to about 0.051 mm. Examples for films as backsheet materials include RR8220 blown films and RR5475 cast films as manufactured by Tredegar Industries, Inc. of Terre Haute, Ind., U.S. The backsheet film is preferably embossed and/or matte finished to provide a more clothlike appearance. Preferably, the backsheet 26 may permit vapors to escape from the absorbent article while still preventing liquid exudates from passing through the backsheet 26.

The absorbent article may further comprise elastification or closure features (not shown if FIG. 1) which are well-known in the art and—for example—described in E 0254476 (Alemany).

The topsheet 24 is positioned adjacent the body surface of the absorbent core 28 and is preferably joined thereto and to the backsheet 26 by attachment means (not shown) such as those well known in the art. Suitable attachment means are described with respect to joining the backsheet 26 to the absorbent core 28. As used herein, the term "joined" encompasses configurations whereby an element is directly secured to the other element by affixing the element directly to the other element, and configurations whereby the element is indirectly secured to the other element by affixing the element to intermediate member(s) which in turn are affixed to the other element.

Generally, the topsheet 24 is compliant, soft feeling, and non-irritating to the wearer's skin. Further, the topsheet 24 is liquid previous permitting liquids (e.g. urine) to readily penetrate through its thickness. A suitable topsheet may be manufactured from a wide range of materials, such as porous foams; reticulated foams; apertured plastic films; or woven or nonwoven webs of natural fibres (e.g., wood or cotton fibres), synthetic fibres (e.g., polyester or polypropylene fibres), or a combination of natural and synthetic fibres. There are a number of manufacturing techniques which may be used to manufacture the topsheet 24. For example, the topsheet 24 may be a nonwoven web of fibres spunbonded, carded, wet-laid, meltblown, hydroentangled, combinations of the above, or the like.

Alternatively, combination composites of both nonwoven and apertured films may be used, and for the hydrophilicity adjustment the respective options of both can be applied.

Preferably, the topsheet pore size should not be smaller than the pores of the underlying layer, such that—in combination with the hydrophilicity of both layers—the fluid within the topsheet can be readily drained towards the underlying layer through the hydraulic forces.

The pore size and pore size distribution of this uppermost layer and its relation to the respective pick up materials is very relevant for the conventional rewet tests, as these generally rely on capillary transport from the absorbent article which is subjected to the testing and the pick-up medium.

The absorbent cores should be generally compressible, conformable, non-irritating to the wearer's skin, and capable of absorbing and retaining liquids such as urine and other certain body exudates. As shown in FIG. 1, the absorbent core 28 has a garment surface ("lower" or "bottom" part), a body surface, side edges, and waist edges. In order to fit best into the overall absorbent article design, the absorbent core 28 may be manufactured in a wide variety of overall sizes and shapes (e.g., rectangular, hourglass, "T"-shaped, asymmetric, etc.) It further might comprise—such as in an acquisition pad (29)—a wide variety of liquid-absorbent materials commonly used in disposable diapers and other absorbent articles such as—but not limited to—comminuted wood pulp which is generally referred to as airfelt; melt-blown polymers including coform; chemically stiffened modified or cross-linked cellulosic fibres; tissue including tissue wraps and tissue laminates.

The configuration and construction of the absorbent core 28 may also be varied (e.g., the absorbent core 28 may have varying caliper zones, a hydrophilic gradient, a superabsorbent gradient, or lower average density and lower average basis weight acquisition zones; or may comprise one or more layers or structures). The total absorbent capacity of the absorbent core 28 should, however, be compatible with the design loading and the intended use of the diaper 20. Further, the size and absorbent capacity of the absorbent core 28 may be varied to accommodate wearers ranging from infants through adults.

Exemplary absorbent structures for use as the absorbent core 28 are described in U.S. Pat. No. 4,610,678 entitled "High-Density Absorbent Structures" issued to Weisman et al. on Sep. 9, 1986; U.S. Pat. No. 4,673,402 entitled "Absorbent Articles With Dual-Layered Cores" issued to Weisman et al. on Jun. 16, 1987; U.S. Pat. No. 4,888,231 entitled "Absorbent Core Having A Dusting Layer" issued to Angstadt on Dec. 19, 1989; and U.S. Pat. No. 4,834,735, entitled "High Density Absorbent Members Having Lower Density and Lower Basis Weight Acquisition Zones", issued to Alemany et al. on May 30, 1989; Also EP 0 640 330 of Bewick-Sonntag et al.; U.S. Pat. No. 5,180,622 (Berg et al.); U.S. Pat. No. 5,102,597 (Roe et al.)

Skin Hydration Value

The present invention is based on the use of a specifically defined index, the Skin Hydration Value, to characterize the absorbent articles of the invention and directly reflect their impact on skin hydration; this index is calculated using the individual Skin Hydration indexes of each of the loading, storage, and chassis area of the absorbent article, which in turn are measured according to specific methods which as described hereinafter.

Generally, an absorbent article can be separated into distinct areas with respect to their functionality, and in relation how these regions are positioned to the various body parts of the wearer.

The loading area is represented by one or more zones, where the body fluids are deposited on. The size of these zone is depending on external factors, namely of the wearer, such as the intended use of the absorbent article or the position of the wearer while the article is being loaded and the like. It also depends on the performance of the absorbent article itself, for example this area will be larger for an article with poor "run-off" or "acquisition" performance, whereby the discharged fluids do not directly penetrate into the absorbent structure, but are distributed on the surface of the absorbent article. From a fluid transport point of view, the loading area is dominated by "flooding" conditions with fluid flowing primarily under gravity driven conditions and relatively large pore capillary transport.

The storage area is represented by one or more zones in which the liquid discharges are firmly bound by capillary and/or osmotic forces. Samples for suitable materials are conventional fluff, superabsorbent materials, or other highly porous materials, including hydrophilic or hydrophilized foam structures. All these have in common, that they retain water as the essential composition of most body fluids firmly preferably also against external pressures, such as applied by the wearer to the article when sitting or when moving.

The chassis area is represented by zones of the absorbent article, which have no significant absorbency function, at least not with regard to the primary loadings fluids such as urine, menstrual fluids or faeces. However, these zones can have an important gasketting function, such at leg opening of the absorbent articles, or at the waist openings. In other embodiments, "belt like" structures around the waist exemplify such regions. In many instances, these regions will comprise a liquid impermeable layer to avoid liquid penetration from the first two zones to the outside, such as to the clothing of the wearer.

When referring to FIG. 1, the loading area can be represented by the area of the acquisition/distribution layer (29), the storage area by the parts of the storage core (28) which are not covered by the acquisition/distribution layer 29, and the chassis or peripheral area corresponds to the area of the topsheet (24) and backsheet (26) circumscribing the absorbent core (28).

The chassis area must meet breathability need, i.e. permeability for gases and/or vapours, with liquid barrier functionality. Conventional liquid barrier materials such as conventional backsheets made of a thin polyethylene film have generally good liquid barrier properties and do protect wearers clothing from wetting through the absorbent article. However, in such chassis areas, such materials prevent the natural evaporation process of the skin and create the risk of occlusion, whereby sweat as released by the perspiration glands cannot evaporate but is retained in the space between the impermeable film and the skin. This generally relatively small and confined volume can be rapidly saturated with moisture, such that further sweat production will soon oversaturate the atmosphere and thus result in liquid moisture. The hydration state of the skin will the quickly increase up to over-hydration. This over-hydrated skin is then prone to redmarking or other undesired effects which can be further enhanced by only low or moderate mechanical irritation.

Apart from occlusion of sweat, a further undesired effect on skin hydration can occur via water vapour transfer, enhanced by thermal gradients, from a generally wetter area to a drier region of the absorbent article. For example, freshly released and hence relatively warm urine might allow evaporative fluid transfer to other parts of the article which are cooler and thus provide a moisture sink. These other parts might of course also be the "chassis zones".

The present invention now allows not only to provide optimal liquid rewet performance in and around said loading and the storage zones, but also provide skin hydration control from all parts of the wearers body which are covered by the absorbent article, including the chassis area.

The absorbent articles herein should have a Skin Hydration Value of less than 1300, preferably less than 600, more preferably less than 300, said Skin Hydration Value being calculating by adding up the individual Skin Hydration Values measured on each area of the article.

The loading area should have a Skin Hydration Value of less than 150, determined according to the following method, which as mentioned above, departs from the known evaluation method and alleviates their drawbacks.

The method herein, whilst still adhering to the principle of measuring the rewetting to a pick up material, does not rely on capillary fluid transport, but primarily on other fluid transfer mechanism simulating the non-porous structure of the skin in a better way.

The key element of the pick up materials according to the new method herein is that the moisture transfer is not based upon capillary fluid transfer, but that moisture mechanism occur very similar to the ones taking place in the human skin. This is achieved by using "hydratable" materials, which on one side have the ability to pick up moisture, but which maintain their generally sheet like structure even at equilibrium saturation, and do not disintegrate upon wetting. Thereby, the moisture pick up is dominated by hydration mechanisms, i.e. in contrast to the mechanisms of porous and/or fibrous structures, the fluid is transferred to the pick-up materials according to the present invention not by capillary transport through said pores, but rather by directly diffusing into the molecular matrix of the pick up materials, and by hydrogen bonding mechanisms dominating the moisture adsorption in these materials.

A preferred material for being used in these tests has now been found in "synthetic skin" as being used for other purposes such as for wound coverings or for sausage or ham encasings can be an extremely sensitive and accurate evaluation tool, if applied together with the appropriate testing protocol.

Such synthetic skin is described in WO 94/04201 assigned to NATURIN GmbH, Germany, with collagen as an essential element. These films are produced starting from bovine skin skives and transforming these into a gel-like dispersion, which then is extruded into thin films with about 12% moisture content. This material has indeed the ability to pick up moisture in a mechanism very close to real living skin, but is readily available with narrow property variability for laboratory testing. A preferred execution of these films is "Collagen Food Film" manufactured and sold by NATURIN under the designation "COFFI". Such embossed films have a basis weight of about 28 g/m2. With a closely monitored moisture content of about 12% by weight, the film material is flexible and easy to handle. Upon further drying, it starts to become brittle. If in contact with moisture—be this in the form of liquid or vapour—the material starts to further soften and swells up to an equilibrium moisture of 150% of its initial weight.

A testing protocol building on these properties has been developed, for example, for evaluation of baby diapers, and more specifically baby diapers of the widely distributed MAXI/MAXI PLUS size (i.e. infants in the weight range from about 8 kg to about 18 kg).

General

All tests are carried out at about 22+/–2° C. and at 35+/–15% relative humidity. The synthetic urine used in the test methods is commonly known as Jayco SynUrine and is available from Jayco Pharmaceuticals Company of Camp Hill, Pa. The formula for the synthetic urine is: 2.0 g: of KCl; 2.0 g/l of Na2SO4; 0.85 g/l of (NH4)H2PO4; 0.15 g/l (NH4)H2PO4; 0.19 g/l of CaCl2; ad 0.23 g/l of MgCl2. All of the chemicals are of reagent grade. The pH of the synthetic Urine is in the range of 6.0 to 6.4.

Acquisition Test

Figure 2:
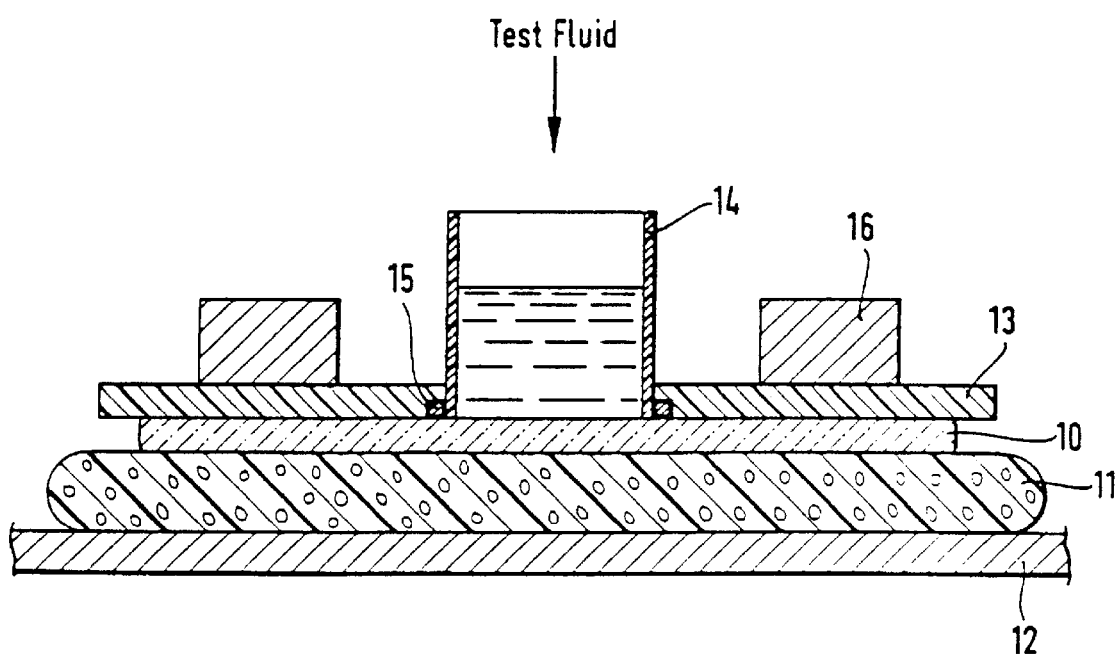
FIG. 2 describes an acquisition test, which can be carried out before the Skin Hydration Value testing.

Referring to FIG. 2, an absorbent structure (10) is loaded with a 75 ml gush of synthetic urine at a rate of 15 ml/s using a pump (Model 7520-00, supplied by Cole Parmer Instruments., Chicago, U.S.A.), from a height of 5 cm above the sample surface. The time to absorb the urine is recorded by a timer. The gush is repeated every 5 minutes at precisely 5 minute gush intervals until the article is sufficiently loaded. Current test data are generated by loading four times.

The test sample, which comprises a core and includes a topsheet and a backsheet, is arranged to lie flat on a foam platform 11 within a perspex box (only base 12 of which is shown). A perspex plate 13 having a 5 cm diameter opening substantially in its middle is placed on top of the sample. Synthetic urine is introduced to the sample through a cylinder 14 fitted, and glued into the opening. Electrodes 15 are located on the lowest surface of the plate, in contact with the surface of the absorbent structure 10. The electrodes are connected to the timer. Loads 16 are placed on top of the plate to simulate, for example a baby's weight. A pressure of 50 g cm-2 (0.7 psi) is typically utilised in this test.

As test fluid is introduced into the cylinder it typically builds up on top of the absorbent structure thereby completing an electrical circuit between the electrodes. This starts the timer. The timer is stopped when the absorbent structure has absorbed the gush of urine, and the electrical contact between the electrodes is broken.

The acquisition rate is defined as the gush volume absorbed (ml) per unit time (s). The acquisition rate is calculated for each gush introduced into the sample. Of particular interest in view of the current invention are the first and the last of the four gushes.

This test is primarily designed to evaluate products having an absorbent capacity of about 300 ml to 400 ml. If products with significantly different capacities should be evaluated, the settings in particular of the fluid volume per gush should be adjusted appropriately to about 20% of the theoretical capacity, and the deviations should be recorded.

Figure 3:
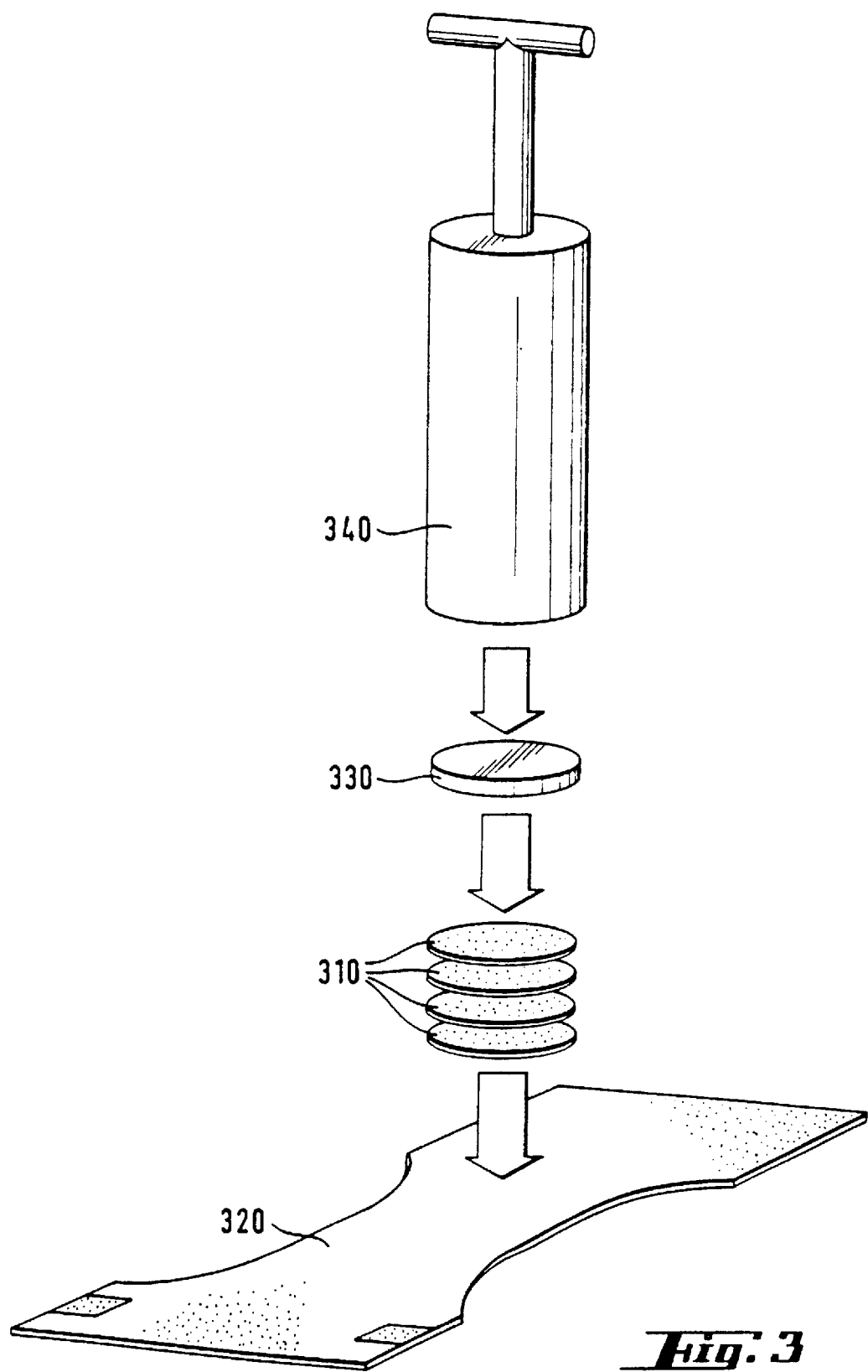
FIG. 3 shows the Skin Hydration Value test set up.

Post Acquisition Collagen Rewet Method (Refer to FIG. 3)

Before executing the test, the collagen film as purchased from NATURIN GmbH, Weinhein, Germany, under the designation of COFFI and at a basis weight of about 28 g/m2 this prepared by being cut into sheets of 90 mm diameter e.g. by using a sample cutter device, and by equilibrating the film in the controlled environment of the test room (see above) for at least 12 hours (tweezers are to be used for all handling of the collagen film). At least 5 minutes, but not more than 6 minutes after the last gush of the above acquisition test is absorbed, the cover plate and weights are removed, and the test sample (320) is carefully placed flat on a lab bench. 4 sheets of the precut and equilibrated collagen material (310) are weighed with at least one milligram accuracy, and then positioned centred onto the loading point of the article, and covered by perspex plate (330) of 90 mm diameter, and about 20 mm thickness. A weight (340) of 15 kg is carefully added (also centred). After 30+/–2 seconds the weight and perspex plate are carefully removed again, and the collagen films are reweighed.

The Post Acquisition Collagen Rewet Method result is the moisture pick up of the collagen film, expressed in mg. Such a result should be inferior to 50 mg, when using the above test, for the loading area of an absorbent article according to the present invention.

The Skin Hydration Value is then calculated by dividing the Post Acquisition Collagen Rewet Method result by the area of the collagen containing film used in the Post Acquisition Collagen Rewet Method and multiplying with the total area of the loading zone of the respective article.

The storage area of the absorbent articles of the invention should have a Skin Hydration Value of less than 20, measured according to the same method as described hereinabove, i. e. using the Post Acquisition Collagen Rewet Method result; such a result for the storage area of the absorbent articles of the invention should be inferior to 5 mg, using the above test.

The chassis area should have a Skin Hydration Value of less than 1250, preferably less than 500, according to the following specific method:

Chassis Collagen Wetness Test

This test is based on similar principles as the Post Acquisition Collagen Rewet Method test outlined above, namely the liquid pick-up and retention capability of Collagen films. It is, however, modified to better reflect the situation in areas of the absorbent article, where no significant absorption capacity is present, and where—in particular when using vapour permeable materials—moisture content of a skin replica material can be reduced by evaporation through the permeable layer.

First, two layers of the film are prepared as for the Post Acquisition Collagen Rewet Method.

A load of about 100 mg of synthetic urine is carefully applied to the first layer whilst avoid run-off, and weighed to an accuracy of 1 mg. The second layer is accurately weighed, too, and placed on to top of the first layer.

Both are then covered with the respective chassis materials, e.g. with a layer of topsheet and a layer of plastic film backsheet in the case of most conventional diapers, or with a layer of hydrophilic topsheet and a layer of hydrophobic nonwoven as backsheet for designs where such a combination can be found in the periphery of diapers.

After 60 minutes waiting time, whereby air convections needs to be minimized such as by placing cylindrical ring of 15 cm diameter and 15 cm height around the sample, the cover layers are removed and the collagen sheets are reweighed.

The result is then corrected for deviations of the added amount from 100 mg (i.e. divided by the actually added weight and multiplied by 100) The final result of the Chassis Collagen Wetness Test is than expressed in mg. For the chassis areas of absorbent articles according to the invention, this value should be inferior to 40 mg, preferably inferior to 30 mg, when using the above test.

The respective chassis Skin Hydration Value can be calculated in analogy to the above procedure, namely dividing the Chassis Collagen Wetness test result by the area of the collagen sheets, and multiplying with the respective area in the absorbent article.

Essentially, good results in this criterion can be reached by either reducing the negative overhydration effects of the individual zones, or by at least minimizing the area of zones with relatively poor performance.

It should be noted, that both a larger and a smaller number of zones can be taken into consideration, and the option of looking at a large number of small areas giving almost a continuous mapping of the properties of the absorbent article should also be regarded as the wider scope of the present description. The most critical distinction, however, needs to remain between zones of the absorbent core and of the chassis or peripheral zone, as there the different method applications need to be applied.

It should be noted further, that this testing protocol can be adjusted easily according to specific product types, such as different baby diaper sizes, or adult incontinence articles, or catamenial articles, or by the variation in the type and amount of loading fluid, the amount and size of the absorbent material, or by variations in the applicable pressure. Having once defined these relevant parameters, such modifications will be obvious to the man skilled in the art. When considering the results from the adjusted test protocol the products can easily be optimizing these identified relevant parameter such as in a designed experiment according to standard statistical methods with realistic in use boundary conditions.

In order to further illustrate the benefits of this new method in assessing absorbent articles, one of the conventional rewet testing protocols has been use as follows:

Comparative Capillary Rewet Test

A comparative test is executed according the following procedure. This test is also carried out 10 minutes (+/−5 sec) after the acquisition test, but uses 10 sheets of blotting paper of 220 g/m2 as supplied by Hollinsworth & Vose, UK under the designation of MEDIUM WHITE W/S, and cut to 20 by 10 cm. This is equilibrated and preweighed, and positioned centred onto the loading point. A circular weight of 4860 g (in total) with a perspex plate of 18 cm by 6 cm is covered with a soft foam of a basis weight of 500 g/m2 of 1 cm thickness and a Polyethylene film is carefully positioned onto the filter paper and left on it for 15 seconds.

The value for rewetting is the weight increase of the blotting papers.

In contrast to the conventional tests, the new testing tool now allows to even distinguish relatively well performing products, i.e. absorbent articles where only a too small amount of liquid will not allow conventional testing tools to discern such products, articles or structures. Consequently, new absorbent articles with the ability to provide unprecedented skin hydration performance can be designed.

Surprisingly, it has been found, that such a performance can be achieved by starting from conventional designs, which however need to be modified in an extreme way, e.g. by increasing the superabsorbent content to extremely high levels. Heretofore, such amounts were not considered to be justified, from an effort to result relation, i.e. the undoubtedly extreme effort was not judged to counterbalance positive effects. These latter, however, were generally based upon conventional (capillary) rewet results, which were not practically not able to discern such products. Of course, the invention should not be viewed to be limited to the use of conventional approaches, but also other designs can be used to achieve the requirements as outlined herein.

Samples according to the invention as well as comparative samples have been submitted to the conventional test protocols as well as to the new Post Acquisition Collagen Rewet Method protocol and the resulting Skin Hydration Values have been determined. Further, some articles have been given to a panel of specially recruited mothers, and their judgment of the performance in particular with respect to skin dryness and skin health condition has been monitored. For especially strenuous wearing conditions, i.e. overnight conditions, additional testing of the skin hydration in the genital region was performed by using a NOVAMETER equipment (as descried in Eisner—see above).

EXAMPLES

In order to further exemplify the benefits of the current invention, samples of different baby diapers have been submitted various test protocols as outlined in the above.

Sample 1 is a commercially available product, PAMPERS Baby Dry Maxi/MAXI PLUS size as marketed by Procter & Gamble in Europe. Sample 3 is a commercially available product, HUGGIES FLEXIFIT as marketed by Kimberly-Clark in Europe Sample 2 is identical to sample 1 except for the following:

First, chemically treated stiffened cellulosic material (CS) supplied by Weyerhaeuser Co., US under the trade designation of "CMC" functioning as an acquisition/distribution layer is doubled in basis weight, by an increase from about 295 g/m2 to 590 g/m2.

Second, an additional acquisition layer in introduced between the topsheet and said chemically treated stiffened cellulose layer, namely a high-loft chemically bonded nonwoven as supplied by FIBERTECH, North America under the designation type 6852. It is a chemically bonded PET fibre web of a basis weight of 42 g/m2 and a width of 110 mm over the full length of the absorbent core.

Thirdly, the cellulose material usage in the storage core underneath the chemically treated stiffened cellulosic material is increased from about 20 g to 40 g per pad.

Fourth, the amount of superabsorbent material in this storage core is increased from about 10 g to about 33 g per pad. Superabsorbent material was supplied by Stockhausen GmbH, Germany under the trade name FAVOR SXM, type T5318.

The results were as follows:

TABLE 1

|  | Sample 1 | Sample 2 | Sample 3 |
|---|---|---|---|
| Post Acquisition Collagen Rewet Method results |  |  |  |
| Loading area rewet [mg] | 80 | 37 | 85 |
| Storage area rewet [mg] | 20 | 2 | 22 |
| Diaper surfaces |  |  |  |
| Loading area [cm2] | 187 | 187 | 198 |
| Storage area [cm2] | 341 | 341 | 463 |
| Skin Hydration Values |  |  |  |
| loading area | 237 | 110 | 267 |
| storage area | 108 | 11 | 162 |

TABLE 1-continued

|  | Sample 1 | Sample 2 | Sample 3 |
|---|---|---|---|
| comparative filter paper |  |  |  |
| rewet protocol [g] | 0.4 | 0.35 | 0.43 |
| Overnight wear study |  |  |  |
| NOVAMETER testing |  |  |  |
| genital area, [-] | 540 | 366 | 548 |
| number of babies tested | 43 | 21 | 20 |
| % of mothers rating skin being . . . |  |  |  |
| dry | 61 | 63 | 55 |
| slightly damp | 29 | 37 | 30 |
| damp | 10 | 0 | 15 |
| wet | 0 | 0 | 0 |
| number of babies tested | 21 | 21 | 20 |

As can be seen from these test, the directional differences between the two reference products could be made significant on a statistical basis, and the test product showed a significant improvement over the other two products.

A further test has been performed to show the advantages of air permeable materials such as for backsheet applications. For this the test as described above was applied to a conventional polyethylene backsheet, and in comparison to a "breathable" backsheet, consisting of a hydrophobic polypropylene non-woven, of 23 g basis weight made by spunbonding technology as supplied by the same supplier as the topsheets described above.

TABLE 2

|  | PE film | PP nonwoven |
|---|---|---|
| Chassis Collagen Wetness test [mg] | 95 | 37.5 |

Clearly, the breathable material exhibits a much lower wetness than the conventional film backsheet material.

For the Products of example 1, containing a conventional backsheet, the chassis Skin Hydration Value was measured, and consequently also the total diaper Skin Hydration value was calculated: Rewets were as follows:

TABLE 3

|  | Sample 1 | Sample 2 | Sample 3 |
|---|---|---|---|
| Chassis area [cm2] | 731 | 731 | 643 |
| Skin Hydration Values |  |  |  |
| chassis area | 1152 | 1152 | 1013 |
| total | 1497 | 1272 | 1442 |

What is claimed is:

1. An absorbent article capable of covering certain parts of a body and comprising distinct areas including a loading area, a storage area, and a chassis area, wherein said article has a Skin Hydration Index Value of less than 1300, calculated based on a summation of individual Skin Hydration Values of said loading area, said storage area, and said chassis area wherein said Skin Hydration Values of said loading area, said storage area, and said chassis area are determined by fluid transfer methods using hydratable collagen film materials and can be expressed in terms of (mg of moisture pick up/area of hydratable collagen film material)× (total area of the loading area, storage area, or chassis area).

2. An absorbent article according to claim 1, wherein said Skin Hydration Value of said absorbent article is less than 600.

3. An absorbent article according to claim 2, wherein said Skin Hydration Value of said absorbent article is less than 300.

4. An absorbent article according to claim 1, wherein said loading area has a Skin Hydration Value of less than 150, calculated based on (mg of moisture pick up/area of hydratable collagen film material)×(total area of the loading area).

5. An absorbent article according to claim 1, wherein said storage area has a Skin Hydration Value of less than 20, calculated based on (mg of moisture pick up/area of hydratable collagen film material)×(total area of the storage area).

6. An absorbent article according to claim 5, wherein said chassis area has a Skin Hydration Value of less than 1250, calculated based on (mg of moisture pick up/area of hydratable collagen film material)×(total area of the chassis area).

7. An absorbent article according to claim 6 wherein said chassis area has a Skin Hydration value of less than 500.

\* \* \* \* \*

UNITED STATES PATENT AND TRADEMARK OFFICE
CERTIFICATE OF CORRECTION

PATENT NO.    : 6,388,166 B1
DATED         : May 14, 2002
INVENTOR(S)   : Mathias Kurt Herrlein et al.

It is certified that error appears in the above-identified patent and that said Letters Patent is hereby corrected as shown below:

Column 1,
Line 12, delete "previous" and insert -- pervious --.
Line 36, delete "There," and insert -- There --.

Column 2,
Lines 15-16, delete ""Bio-engineering of the: Water and Stratum Corneum"," and insert -- "Bio-engineering of the skin: Water and Stratum Corneum", --.

Column 4,
Lines 21 and 41, delete "previous" and insert -- pervious --.

Column 5,
Line 41, delete "if" and insert -- in --.
Line 58, delete "previous" and insert -- pervious --.

Column 8,
Line 59, delete "28 g/m2" and insert -- 28 g/m$^2$ --.

Column 9,
Line 10, delete "2.0 g:" and insert -- 2.0 g --.
Line 11, delete "Na2SO4;" and insert -- $Na_2SO_4$; --.
Lines 11 and 12, delete "(NH4)H2PO4;" and insert -- $(NH_4)H_2PO_4$; --.
Line 12, delete "CaCl2;" and insert -- $Cacl_2$; --.
Line 12, delete "MgCl2." and insert -- $MgCl_2$. --.
Line 61, delete "28 g/m2" and insert -- 28 g/m$^2$ --.

Column 11,
Line 46, delete "500 g/m2" and insert -- 500 g/m$^2$ --.

Column 12,
Line 16, delete "descried" and insert -- described --.
Line 16, delete "Eisner" and insert -- Elsner --.
Line 34, delete "295 g/m2" and insert -- 295 g/m$^2$ --.
Line 34, delete "590 g/m2" and insert -- 590 g/m$^2$ --.
Line 41, delete "42 g/m2" and insert -- 42 g/m$^2$ --.
Lines 62 and 63, delete "[cm2]" and insert -- [cm$^2$] --.

UNITED STATES PATENT AND TRADEMARK OFFICE
CERTIFICATE OF CORRECTION

PATENT NO. : 6,388,166 B1
DATED : May 14, 2002
INVENTOR(S) : Mathias Kurt Herrlein et al.

It is certified that error appears in the above-identified patent and that said Letters Patent is hereby corrected as shown below:

<u>Column 14,</u>
Line 5, delete "[cm2]" and insert -- [cm$^2$] --.
Lines 25 and 28, delete "Hydration" and insert -- Hydration Index --.

Signed and Sealed this

Fourth Day of April, 2006

JON W. DUDAS
*Director of the United States Patent and Trademark Office*